United States Patent
Butler

(10) Patent No.: US 11,282,202 B2
(45) Date of Patent: Mar. 22, 2022

(54) TEMPORAL CALIBRATION OF AN ANGIOGRAPHIC IMAGING SYSTEM

(71) Applicant: William E. Butler, Boston, MA (US)

(72) Inventor: William E. Butler, Boston, MA (US)

(*) Notice: Subject to any disclaimer, the term of this patent is extended or adjusted under 35 U.S.C. 154(b) by 0 days.

(21) Appl. No.: 16/813,513

(22) Filed: Mar. 9, 2020

(65) Prior Publication Data
US 2020/0286237 A1    Sep. 10, 2020

Related U.S. Application Data

(60) Provisional application No. 62/815,476, filed on Mar. 8, 2019.

(51) Int. Cl.
*G06K 9/00* (2006.01)
*G06T 7/00* (2017.01)
*A61B 90/00* (2016.01)
*A61B 6/00* (2006.01)
*G06T 1/00* (2006.01)
(Continued)

(52) U.S. Cl.
CPC ............ *G06T 7/0016* (2013.01); *A61B 6/504* (2013.01); *A61B 6/5294* (2013.01); *A61B 90/39* (2016.02); *G06T 1/0085* (2013.01); *G06T 11/005* (2013.01); *G16H 30/20* (2018.01); *G16H 30/40* (2018.01); *A61B 2090/3966* (2016.02);
(Continued)

(58) Field of Classification Search
CPC ... G06T 7/0016; G06T 1/0085; G06T 11/005; G06T 2211/404; G06T 2207/10116; A61B 90/39; A61B 6/5294; A61B 6/504; A61B 2090/3966; A61B 6/582; A61B 6/486; A61B 6/487; A61B 6/468; G16H 30/20; G16H 30/40; G06K 2209/03; G06K 2209/05
See application file for complete search history.

(56) References Cited

U.S. PATENT DOCUMENTS 4,698,836 A    10/1987  Minasian
4,896,344 A *  1/1990  Grady ..................... A61B 6/06
                                                        378/146
(Continued)

OTHER PUBLICATIONS

International Search Report and Written Opinion received in international application No. PCT/US2020/021754, dated Jun. 9, 2020 (8 pages).
(Continued)

*Primary Examiner* — Shervin K Nakhjavan
(74) *Attorney, Agent, or Firm* — Edell, Shapiro & Finnan, LLC

(57) ABSTRACT

Angiographic data is obtained by injecting a chemical contrast agent intravascularly, and imaging passage of the contrast as a function of time, thereby generating a sequence of images. To correct error from uncalibrated timestamps embedded in the image metadata, radio-opaque markers are used to generate a watermark embedding timestamp data in obtained images. The radio-opaque markers cause opacification on the x-ray images in the form of dynamic watermarks that encode timestamps. The positions of the markers in the watermark (cast from the radio-opaque markers) are then processed and analyzed to generate an accurate timestamp for the image. By generating an accurate timestamp, synchronized calculations of the images with other data sources are provided.

23 Claims, 7 Drawing Sheets

(51) Int. Cl.
*G16H 30/20* (2018.01)
*G16H 30/40* (2018.01)
*G06T 11/00* (2006.01)

(52) U.S. Cl.
CPC .............. *G06T 2207/10116* (2013.01); *G06T 2211/404* (2013.01)

(56) References Cited

U.S. PATENT DOCUMENTS

| | | | | |
|---|---|---|---|---|
| 5,090,042 | A * | 2/1992 | Bejjani | A61B 5/1128 348/E5.086 |
| 6,267,502 | B1 * | 7/2001 | McNeirney | A61B 6/08 378/205 |
| 6,359,960 | B1 * | 3/2002 | Wahl | G06T 7/70 378/20 |
| 8,326,403 | B2 * | 12/2012 | Pescatore | A61B 6/12 600/426 |
| 10,123,761 | B2 | 11/2018 | Butler | |
| 10,653,379 | B2 | 5/2020 | Rapoport | |
| 11,123,035 | B2 | 9/2021 | Butler et al. | |
| 2005/0080327 | A1 | 4/2005 | Jenkins | |
| 2005/0147206 | A1 * | 7/2005 | Skalli | A61B 6/584 378/41 |
| 2007/0071176 | A1 * | 3/2007 | Main | A61N 5/1048 378/207 |
| 2007/0238947 | A1 * | 10/2007 | Pescatore | A61B 6/583 600/407 |
| 2007/0276243 | A1 * | 11/2007 | Gerard | A61B 8/4245 600/440 |
| 2008/0021297 | A1 * | 1/2008 | Boosten | A61B 8/5276 600/374 |
| 2008/0025475 | A1 * | 1/2008 | White | A61B 6/4283 378/208 |
| 2008/0045827 | A1 * | 2/2008 | Rongen | A61B 6/469 600/407 |
| 2009/0086924 | A1 * | 4/2009 | Wang | G03B 42/02 378/165 |
| 2011/0228906 | A1 * | 9/2011 | Jaffray | A61B 6/032 378/65 |
| 2012/0093285 | A9 | 4/2012 | Ren | |
| 2012/0093386 | A1 | 4/2012 | Devadas | |
| 2013/0051528 | A1 | 2/2013 | Inglese | |
| 2013/0121551 | A1 * | 5/2013 | Poulsen | G06T 17/00 382/131 |
| 2013/0184571 | A1 * | 7/2013 | Wilkening | A61B 5/066 600/426 |
| 2016/0073885 | A1 * | 3/2016 | Adler | A61B 6/582 600/427 |
| 2016/0166333 | A1 * | 6/2016 | Wang | A61B 90/11 600/476 |
| 2018/0333131 | A1 * | 11/2018 | Lin | A61B 6/06 |

OTHER PUBLICATIONS

Murphy, "Tracking Moving Organs in Real Time," Seminars in Radiation Oncology, vol. 14, No. 1, Jan. 2004 (10 pages).
DICOM Standards Committee, "NEMA PS3 / ISO 12052: Digital Imaging and Communications in Medicine (DICOM) Standard," 2014, accessed online on Jun. 15, 2020 at: <http://dicom.nema.org/medical/dicom/current/output/html/part14.html> (63 pages).
U.S. Appl. No. 62/801,780, filed Feb. 6, 2019 (33 pages).
Pi Plates code website, accessed online on Jun. 15, 2020 at <https://pi-platescomcode#Object_Oriented_MOTORplate_Demo_Using_Tkinter> (7 pages).
Pololu Robotics & Electronics Website for Stepper Motor: Bipolar, 200 Steps/Rev, 20x30mm, 3.9V, 0.6 A/Phase, accessed online on Jun. 15, 2020: <https://www.pololu.com/product/1204> (4 pages).
Pi Plates product information for MOTORplate, accessed online on Jun. 15, 2020 at: <https://pi-plates.com/motorr1/> (3 pages).
Raspberry Pi 4 website home page, accessed online on Jun. 15, 2020 at <https://www.raspberrypi.org/> (11 pages).
NIST Time and Frequency Services website, accessed online on Jun. 15, 2020 at <https://www.nist.gov/pml/time-and-frequency-division/services/internet-time-service-its> (8 pages).
Schumacher, "Analog Clock and Watch Reader," 2015, pp. 1-10 (https://www.cs.bgu.ac.il/~ben-shahar/Teaching/Computational-Vision/StudentProjects/ICBV151/ICBV-2015-1-ChemiSchumacher/Report.pdf).

* cited by examiner

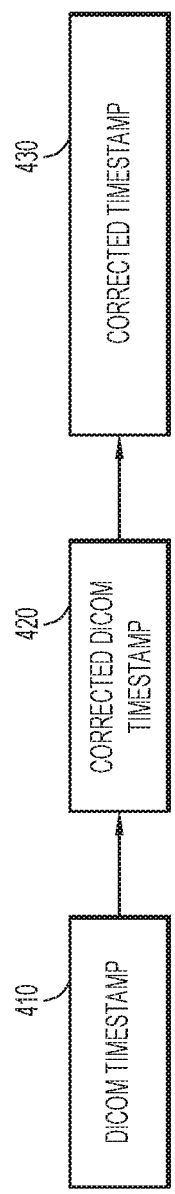
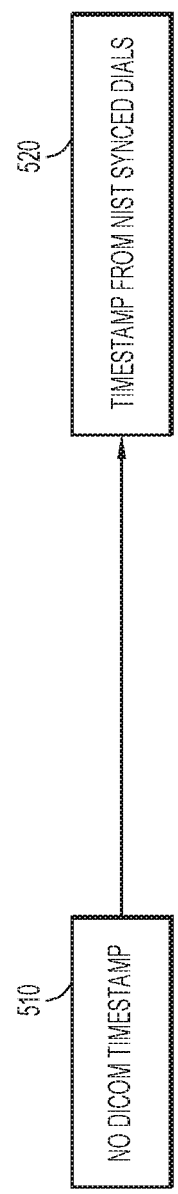

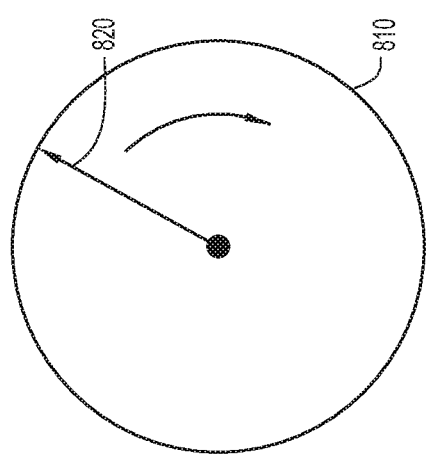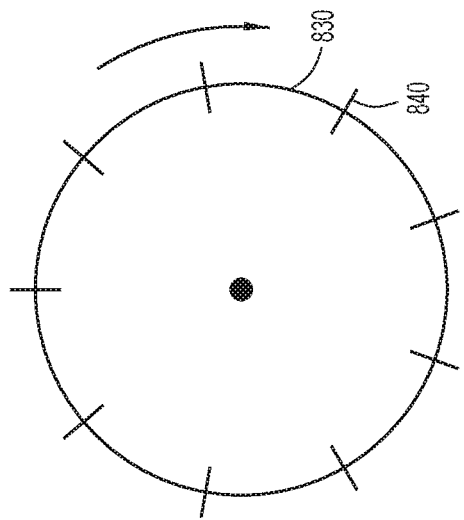

TEMPORAL CALIBRATION OF AN ANGIOGRAPHIC IMAGING SYSTEM

CROSS-REFERENCE TO RELATED APPLICATIONS

This application claims priority to U.S. Provisional Application No. 62/815,476, filed Mar. 8, 2019, the contents of which are hereby incorporated by reference in their entirety.

FIELD OF THE INVENTION

The field is directed towards an angiographic or other x-ray imaging system that generates a timestamp, and in particular, an angiographic or other x-ray imaging system that generates an accurate timestamp with sub-second precision to allow synchronization with an external signal.

BACKGROUND OF THE INVENTION

The manufacturers of angiographic acquisition equipment did not foresee a need for including accurate timestamps on angiographic images. Timestamps stored as metadata in angiographic images show error ranging from seconds to minutes. Current angiographic imaging systems do not include a mechanism, such as an application programming interface, to recalibrate the system timestamp.

A common file format for angiographic images uses a DICOM standard, in which each image of a series of angiographic images includes a header with DICOM metadata. While the DICOM metadata includes a tag for storage of timestamp information, the stored timestamp has been determined to be incorrect and does not indicate the correct time at which the corresponding angiographic image is acquired.

Additionally, existing angiographic equipment does not include a hardware input port for synchronization with an external signal, such as a cardiac signal. Further, such equipment does not have an internal database or file structure for unified storage of an external cardiac signal and angiographic images.

While cardiac gated images obtained using computed tomography and MRI offer post hoc association of the timing of computed tomography or MRI data with an external signal, this equipment has been manufactured to include design specifications allowing the synchronization of internal clocks of the computed tomography or MRI hardware with the external signal. However, those types of systems would not work for angiographic systems lacking hardware or software for synchronization of an internal clock.

Accordingly, techniques are needed for obtaining accurate timestamps in angiographic and other x-ray imaging systems lacking internal clock synchronization.

SUMMARY OF THE INVENTION

Present techniques are directed to systems, methods, and computer readable media for generating an accurate timestamp with sub-second precision in an x-ray imaging system such as an angiographic imaging system with an internal clock that is not synchronized to a time standard (e.g., such as a global or international time standard, a National Institute of Standards and Technology (NIST) time standard, or any other suitable time standard), allowing the images obtained by the imaging system to be synchronized to an external signal.

A plurality of movable radio-opaque markers are positioned between a radiation emitter and a radiation detector array. Each of the plurality of radio-opaque markers are caused to move at a respective frequency. While the radio-opaque markers are moving, a series of x-ray images is obtained, each image comprising a dynamically generated watermark cast by the plurality of moving radio-opaque markers, wherein a position of each radio-opaque marker is shown on the watermark. The series of images are processed to measure a rotational position of each of the plurality of marks of the watermark. Based on the measured rotational position of the marks and the respective frequency of each of the plurality of radio-opaque markers, a timestamp is determined.

In aspects, the watermark encodes a timestamp with sub-second precision. In aspects, each of the plurality of radio-opaque markers are rotating at a rate determined by a controller synchronized to a time standard.

In aspects, a metadata timestamp is corrected based on the timestamp encoded by the watermark.

In aspects, each of the plurality of stepper motors rotate at a different specified frequency so as to cause an associated radio-opaque marker to rotate at the same frequency. In aspects, at least two radio-opaque markers are used to obtain sub-second precision.

In aspects, a timestamp generated as provided herein may be used to synchronize the images with an external signal, in techniques for spatiotemporal reconstruction of cardiac frequency phenomena from angiographic images acquired at faster than cardiac rate (see, U.S. Pat. No. 10,123,761, issued on Nov. 13, 2018, which is incorporated by reference herein in its entirety).

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components.

FIG. 4 is a flowchart for generating a timestamp from correcting the metadata timestamp based on the processed dynamically watermarked x-ray images, according to the techniques provided herein.

FIG. 5 is a flowchart for generating a timestamp from the processed dynamically watermarked x-ray images, according to the techniques provided herein.

FIGS. 8A and 8B show examples of different type of dials, according to the techniques provided herein.

DETAILED DESCRIPTION

Figure 1:
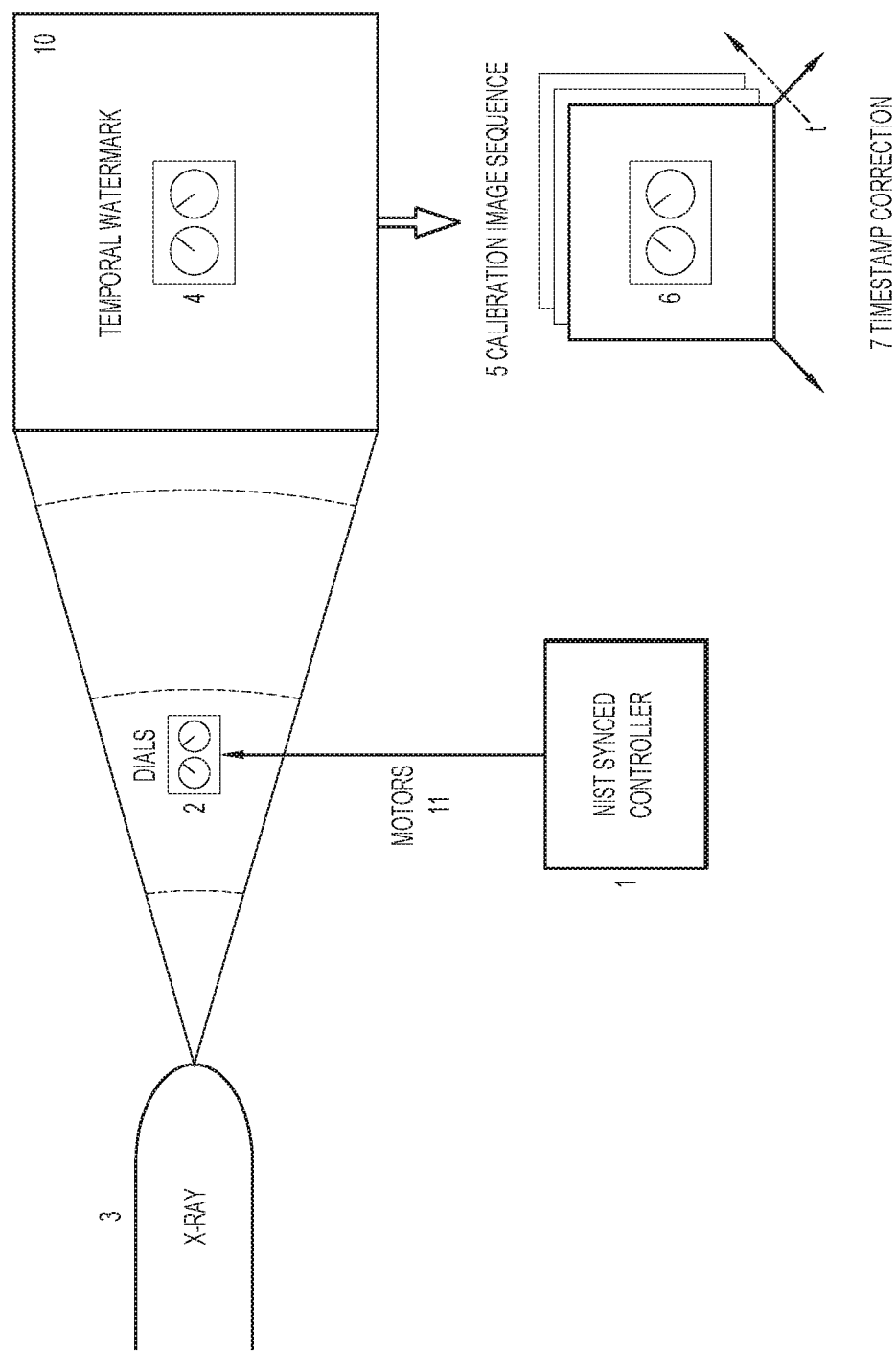
FIG. 1 illustrates an angiographic system for generating accurate timestamps, based on dynamic watermarking of x-ray images, according to the techniques provided herein.

An angiographic imaging system comprises hardware that includes an x-ray emitter, an x-ray detector array, and electronic hardware and software that translate the data captured by the x-ray detector array into an image. To obtain an angiogram, a bolus of a chemical contrast agent is injected intravascularly into a patient, and a sequence or time series of x-rays is obtained. Two-dimensional projections of the anatomy of the vascular system are captured as the chemical contrast agent, which blocks the passage of x-rays, passes through the vascular system in the x-ray projection path.

The bolus passage timing of the chemical contrast agent may offer medical information. For example, images acquired relatively early in the bolus passage are more likely to reflect arterial anatomy, and those acquired relatively late are more likely to reflect venous anatomy. The aggregation of these images, sequenced according to time of acquisition, comprises an angiogram.

Each image has a timestamp corresponding to the moment in time that the signal produced by the x-ray signal detector array is aggregated into a digitized image. This timestamp may be stored in metadata. A common image file format for x-ray and other medical images uses a DICOM standard. This standard provides a timestamp tag, included as metadata, to indicate the moment of acquisition of the x-ray image.

However, angiographic imaging systems are typically closed systems that do not permit calibration of internal clocks. As a result, the x-ray image timestamps, as extracted from image metadata, are often unsatisfactory for other applications, such as synchronizing the images with other time series data for computational purposes.

In some cases, measurements in timestamp error have revealed errors of up to twenty minutes or more. Additionally, the DICOM standard does not provide sufficient temporal resolution (e.g., sub-second resolution) to allow the angiographic images to be accurately synced with external signals (e.g., a cardiac signal).

Present techniques provide for generating an accurate timestamp based on a plurality of radio-opaque markers synced to a NIST time standard that are used to form a watermark, the watermark cast by the plurality of radio-opaque markers. In some aspects, the DICOM timestamp undergoes a corrective process, based on information provided by the radio-opaque markers. In other aspects, the timestamp is produced solely from information provided by the radio-opaque markers, without utilizing the DICOM timestamp.

With an accurate timestamp, the angiographic data may be synchronized with an external signal, such as a cardiac signal produced by a finger pulse oximeter or by an electrocardiogram. In embodiments, the cardiac signal may be combined with a wavelet algorithm (in some cases cross-correlated) to produce a spatiotemporal reconstruction of individual moving vascular pulse waves from the angiographic image sequence, e.g., as disclosed in U.S. Pat. No. 10,123,761 which is incorporated herein by reference above.

Additionally, the external signal with the wavelet algorithm increases the signal to noise ratio of an angiographic image sequence.

As described below, an apparatus, methods, and computer readable media are provided for inserting into the pixels of an angiogram, a dynamically generated watermark that encodes information that may be converted into a timestamp (e.g., by automated software).

Referring to FIG. 1, a system/device is shown for generating accurate timestamps based on dynamic watermarking of x-ray images, according to the techniques provided herein. In this example, the x-ray source 3 and the x-ray detector array 10 are part of an angiographic imaging system that does not offer the ability to directly calibrate its internal clock or otherwise generate an image with an accurate timestamp.

The system includes a computer (shown in FIG. 7 at computing system 80), a controller 1 and motors 11 (e.g., stepper motors, etc.), radio-opaque dials 2, an x-ray source 3, and an x-ray detector array 10. In this example, x-ray detector 10 shows an embedded temporal watermark 4, from the projection of x-rays onto radio-opaque dials 2. In this example, the radio-opaque marker is in the form of a dial.

In operation, this system generates a calibration series or sequence of images 5, which may undergo processing to convert watermarks 6 within the images into a timestamp correction 7 for the images. Timestamp correction 7 may include an error signal with which to correct the metadata, or a timestamp to replace the metadata. These components are described further below.

The computer may include any suitable computing system, including a stand-alone computer, a server, tablet, laptop, etc. For example, the computer may include a small portable computer that is not in the line of sight between the x-ray source 3 and the x-ray detector array 10 that is used to generate the series of x-ray images.

The computer may be configured to rotate the motors controlling rotation or movement of the radio-opaque markers at specified frequencies. For example, the portable computer may be attached to a controller programmed using a python library for controlling motors. The python library is programmed to turn each motor at a predetermined programmed rate.

A plurality of movable radio-opaque markers (e.g., dials 2), in a radio-opaque reference marker system as shown in FIG. 1, are provided whose relative positions on an x-ray image encode the x-ray image acquisition timestamp. In aspects, the radio-opaque reference marker system includes any system capable of controlling rotation of the radio-opaque markers. By way of example, the movable radio-opaque markers may be in the form of a dial synced to a time standard by a controller. Movement of the radio-opaque markers may be in reference to any suitable coordination system (e.g., an angular coordinate system, an x-y coordinate system, etc.). The relative positions of the radio-opaque markers relative to a radio-opaque reference system are cast as a dynamic watermark on an x-ray image. For example, a radio-opaque marker may be cast as a corresponding mark (as part of a watermark) in the image.

In one embodiment, as shown in FIG. 8A, the movable radio-opaque marker may be in the form of a hand 820 that rotates about the center of a circular frame 810. In this aspect, the frame of the dial is fixed, and rotation of the hand is controlled by the controller. A plurality of dials may be implemented in this manner to achieve the proper temporal resolution.

In another embodiment, as shown in FIG. 8B, the movable radio-opaque marker may include the face of the dial itself, which may be configured to rotate about a center of the face or some other point. In this embodiment, the radio-opaque markers 840 are positioned on the rotating face 830 (e.g., in the form of tick marks, or other suitable form, etc.).

In each case, one or more motors may be used to rotate the movable radio-opaque marker (e.g., by rotating the movable hand or the movable face) of the dial. In an example, rotation of the radio-opaque marker in the form of a dial is driven by a separate motor. In other examples, a single motor may be coupled to a plurality of dials via gears that result in different rotational frequencies. In an aspect, the motor may be directly connected to the dial. In another aspect, the motor may be connected to the dial via one or more connecting components.

Accordingly, while the device is described with respect to rotation of the dial, which includes various forms as provided throughout, it will be understood that the timing is encoded by radio-opaque markers. Thus, present embodiments encompass any suitable form in which a movable radio-opaque marker, e.g., controlled by a controller, encodes temporal information. The radio-opaque marker may include the form of a dial.

The motors, controlled by a controller, may control the dials 2 to move in clicks or in a smooth sweep or any other suitable manner to rotate at specified frequencies while the sequence of x-ray images is obtained. The dials are placed in the line of sight between the x-ray source 3 and the x-ray detector array 10. In aspects, the dials may be placed in a metal mounting bracket, and have metallic hands attached to rotatable shafts. The metallic hands are radiopaque, and appear, e.g., as marks, in the x-ray image. In other aspects, the face of the dial may rotate, and radio-opaque markers may be arranged in a pattern on the face of the dial, wherein the pattern allows timing information to be encoded based upon rotation of the face. In other aspects, the radio-opaque marker may be made of other types of radio-opaque materials, or non radio-opaque materials covered or coated with radio-opaque paint. The pixels corresponding to the x-rays traveling from the x-ray tube 3 onto the x-ray detector array 10 are opacified, forming a watermark in the detector array 10 of an image. The techniques provided herein encompass attachment of the dial (e.g., a metallic or radio-opaque marker) directly to the motor as well as connection of the dial through one or more connecting devices to the motor.

With the motors and their respective dials rotating at programmed rates, a sequence of angiographic images is obtained. In some cases, the images are obtained with the same duration and image frame rate as typically used with an angiographic image series. The radio-opaque markers on the dial are opaque to x-rays, and when images are collected with the dials in the x-ray source pathway, watermarks comprising marks corresponding to the positions of the radio-opaque markers are formed on the image.

Thus, the watermark is produced by a device, such as one or more dials/rotatable radio-opaque marker(s), each radio-opaque marker rotating at a specified frequency and synchronized directly or indirectly to a controller. In some aspects, the controller may be synchronized to a NIST timestamp standard (e.g., by a NIST synced controller). However, present techniques may be used for synchronization to any suitable time standard. The watermark from the radio-opaque marker is embedded into pixels of the angiogram and may be converted into a form that may be compared to the timestamp in the image metadata. This may be used to determine a timestamp correction that may be applied to the metadata (e.g., DICOM timestamp) of the sequence of images, or be converted into a timestamp independently from the image metadata.

Any suitable number of radio-opaque markers or dials may be used, with each dial of the plurality of dials rotating the radio-opaque markers at any suitable frequency to produce a watermark that encodes temporal information. In particular, the number of dials and frequency of rotations of the radio-opaque markers may be configured to encode a timestamp with a specified resolution. A greater number of motors and dials may be employed at designated frequencies (a time period of oscillation), to provide hour, minute, second, and sub-second resolution. At least two motors may be employed at designated frequencies, to provide minute and second resolution.

By way of a non-limiting example, a small portable computer (e.g., Raspberry Pi 3, https://www.raspberrypi.org, Linux operating system) not in the line of sight between the x-ray source and the x-ray detector array, is attached to a hardware unit (e.g., PiPlates Motorplate-R1.0 https://pi-plates.com/motorr1/) that drives digital stepper motors. A set of two stepper motors (e.g., Pololu part number SY20STH30-0604A https://www.pololu.com/product/1204) are placed in the line of sight between the x-ray source and the x-ray detector array. The stepper motors are placed in a metal mounting bracket, and have metallic hands attached to the shaft that act as timing hands.

The stepper motor control unit uses a python library for controlling the stepper motors (https://pi-plates.com/code/#Object_Oriented_MOTORplate_Demo_Using_Tkinter), and is programmed to turn the stepper motor dials at the programmed rates. One of the stepper motor dials is programmed to complete one cycle every 10 seconds, and the other is programmed to complete one cycle per second. The metallic hands are opaque to x-rays and cast a shadow on the x-ray detector array, allowing for an image impression of two dial hands on the image.

In some aspects, the angiographic images (including watermarks) are obtained when a human is not being angiographically imaged. In this case, the timestamp correction is stored in computer memory or in a computer database for subsequent correction of timestamps of human clinical angiograms. A set of calibration timestamps may be obtained before and/or after an angiographic study with a human patient to verify that the timestamp correction has not significantly drifted during the course of a day or week or longer. The calibration may be performed before and/or after a human clinical angiogram.

In other aspects, the angiographic image series are obtained at the same time an angiographic image is obtained for a human, but the position of the dials are placed such that the resultant watermark does not obscure information relevant to the angiogram. Thus, images may be calibrated during a human clinical angiogram by placing the dial apparatus out of the line of x-ray projection of the relevant human anatomy under study.

Thus, this approach functions independently of the angiographic imaging system. The sequence of calibration x-ray images 5 is exported for further analysis, such as the process described in FIG. 2 or FIG. 3 (inclusive of software programs running in a computer) for generation of a time stamp (e.g., by image processing techniques or by a machine learning system) based on the position of the radio-opaque markers cast to form a watermark (e.g., comprising a series of marks corresponding to the radio-opaque markers).

Figure 2:
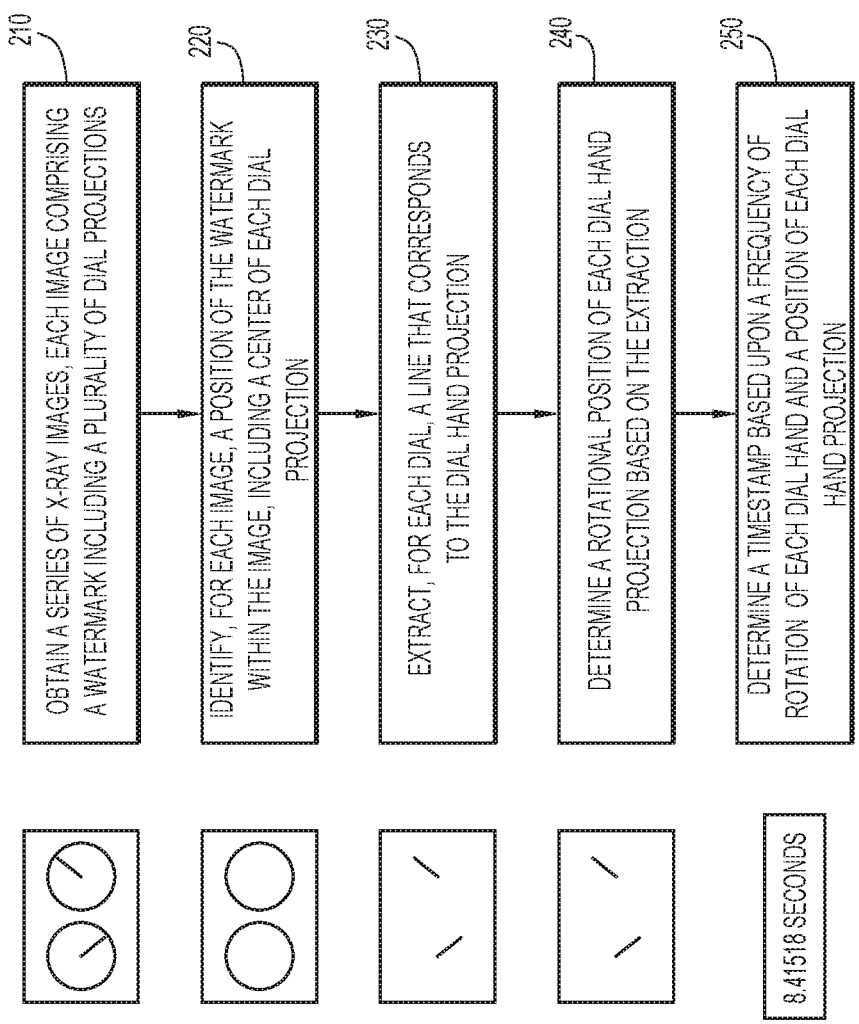
FIG. 2 is a flowchart for processing dynamically watermarked x-ray images using image processing techniques, according to the techniques provided herein.
Figure 3:
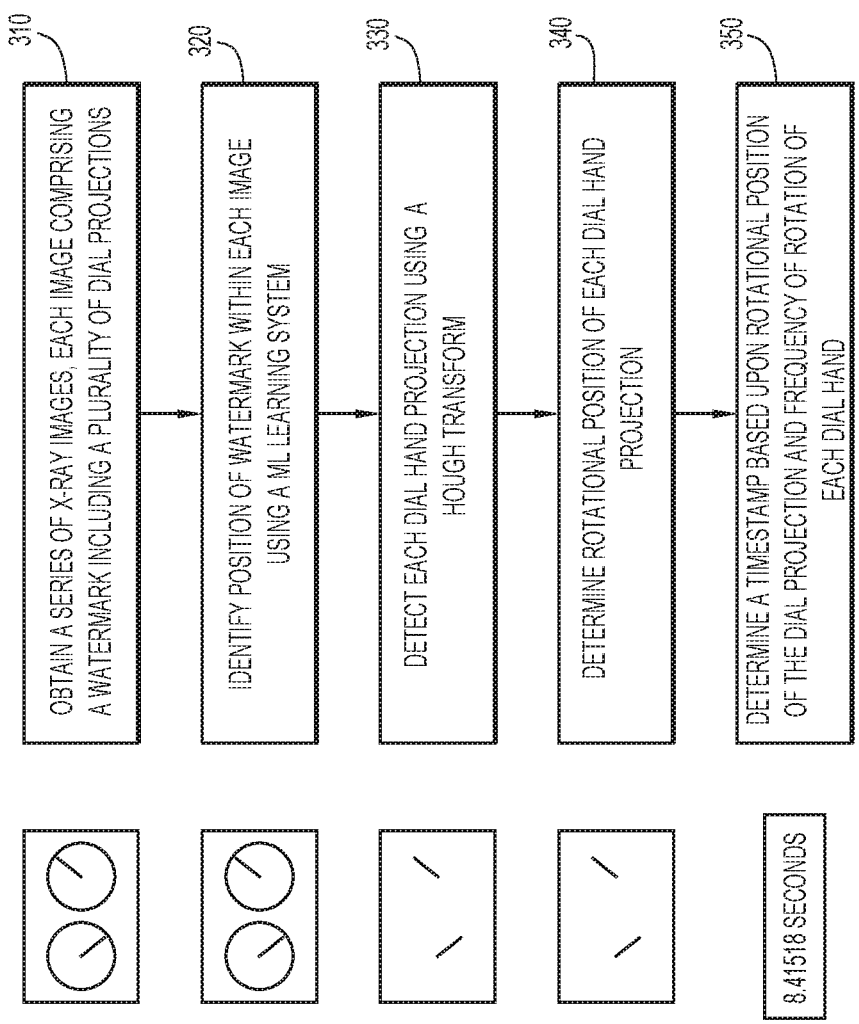
FIG. 3 is a flowchart for processing dynamically watermarked x-ray images using machine learning in combination with image processing techniques, according to the techniques provided herein.

The examples provided in FIGS. 2 and 3 are in reference to a dial comprising a non-movable frame with a rotating dial hand. In this example, the radio-opaque marker is in the form of a dial. However, these techniques are extendable to other dial forms, such as a rotating face of a dial as provided herein, or any other form in which a radio-opaque marker is controlled by a controller and timing is encoded by a watermark cast by the plurality of moving radio-opaque markers onto the x-ray image.

FIG. 2 is a flowchart for processing dynamically watermarked x-ray images using image processing techniques to obtain a timestamp, according to the techniques provided herein. A watermark may be identified, and the encoded timestamp may be decoded based on the position of the dial hand projection and frequency of rotation of the dial hand. In this example, the radio-opaque marker comprises a dial hand. The radio-opaque dial hand is cast onto the x-ray image as a mark/projection, in this case, having the shape of the dial hand.

At operation 210, a series of x-ray images is obtained, each image comprising a watermark generated by casting of one or more radio-opaque dial hands. The watermark encodes information corresponding a timestamp. In this example, the dials may be positioned such that watermarks are generated near a corner of the image, or in a region not including relevant medical information. As shown in this example, the border of the dial may also be optionally in the watermark, by suitable placement of metal.

At operation 220, for each image, a position of the watermark within the image is obtained, including a center of each dial projection. For example, image analysis software may be configured to identify circular shapes, and to identify the center of each identified circle. In other aspects, the location of the watermark (one or more lines) may be provided to the image analysis software. A reference mark may also be included to indicate a proper orientation of the image (e.g., the image may be analyzed when the reference mark is positioned in the upper right corner of an image, to indicate that the overall image has not been rotated or transposed). In some aspects, the dial projections may appear in the image at a predetermined size, and the image analysis system may be configured to identify circles of a predetermined radius.

At operation 230, for each dial, a morphological analysis is performed to extract a line corresponding to each dial hand projection. Morphological analysis may be used to identify lines corresponding to projected dial hands. In some aspects, the identified lines may be stored in memory as vectors. Any suitable function may be used for extraction.

At operation 240, a rotational position or orientation of each dial hand projection/mark is determined based on the extraction. For example, the rotational position of the dial hand projection may be determined by the angle between the current position of the dial hand projection and a position of the reference known to correspond to the start of rotation (0°) of a 360° cycle. In some aspects, the orientation of the vectors may be computed in radians.

At operation 250, a timestamp is determined based upon a frequency of rotation of the dial hand and the rotational position of each dial hand projection. For example, the rotational position (in radians) may be converted into a timestamp based on the known frequency of rotation and conversion factors as shown below.

For example, for a first dial hand, rotating at 1/10 Hz (1 cycle every 10 seconds), the timing in seconds may be determined based on:

10.*dial1Position1/2.Pi

For a second dial hand rotating at 1 Hz (1 cycle every second), the timing in seconds may be determined based on:
1.*dial2Position2/2.Pi The final time in seconds may be determined by combining the two times:

10. * dial1Position1/2.Pi+1.*dial2Position2/2.Pi

In other aspects, the timestamp may be determined based upon values obtained from a lookup table (e.g., relating the rotational position of each dial hand to a timestamp value) wherein the lookup table is frequency specific to the dial hands.

In general, any number of dials may be used to achieve a desired temporal resolution. By way of example, FIGS. 2 and 3 refer to a system with two dials. However, in other cases, three, four, five, six, seven, eight or more dials may be used. Each dial may be configured to rotate at a predetermined frequency of rotation. By way of example, a first dial may be configured to rotate at 10 revolutions per second, a second dial may be configured to rotate at 1 revolution per second, a third dial may be configured to rotate at 1 revolution per 10 seconds. Such a configuration may allow accuracy to be obtained at both the minute and sub-minute scale with high precision.

FIG. 3 is a flowchart for processing dynamic timestamp watermarking of x-ray images using machine learning in combination with image processing techniques, according to the techniques provided herein. Machine learning methods may be employed to automate the identification of the watermark (encoding a timestamp) within an image. Once identified, the encoded timestamp may be decoded based on position of the dial projections and frequency of rotation of the dials.

At operation 310, a series of x-ray images is obtained, each image comprising a watermark including a plurality of dial projections. In this example, the dials may be positioned such that watermarks are generated near a corner of the image, or in a region not including relevant medical information. A reference mark may also be included to indicate a proper orientation of the image (e.g., the image may be analyzed when the reference mark is positioned in the upper right corner of an image, to indicate that the overall image has not been rotated or transposed). At operation 320, a position of a watermark is identified within each image using a machine learning (ML) system. At operation 330, each dial hand projection is detected using a Hough transform or other suitable transform for detecting lines. At operation 340, the rotational position of each dial hand projection (e.g., line from the Hough transform) is determined. For example, the rotational position of the dial hand projection may be determined by the angle between the current position of the dial hand projection and a position of the reference known to correspond to the start of rotation (0°) of a 360° cycle. At operation 350, a timestamp is determined based upon the rotational position of the dial projection and frequency of rotation of each dial hand. In other aspects, the timestamp may be determined based upon values obtained from a lookup table, e.g., relating the rotational position of each dial hand projection to a timestamp value, wherein the lookup table is frequency specific to the dials.

FIG. 4 is a flowchart for generating a timestamp by correction of the metadata timestamp based on watermarked images, according to the techniques provided herein.

A series of images may be obtained from an angiographic study according to FIG. 1, wherein each image comprises a dynamically generated watermark and is associated with a header, including a tag corresponding to a metadata timestamp, including at least an hour and a minute. In this example, timestamp metadata 410, which may be provided in a DICOM format, is embedded in image metadata by existing angiographic imaging systems. The DICOM format includes a metadata tag (timestamp) indicating the moment of acquisition of each image. However, the DICOM timestamp is incorrect.

Corrected DICOM timestamp images 420 are generated by determining an error, and correcting the timestamp of each DICOM timestamp image 410 by the error. For example, the DICOM metadata timestamp is extracted from an image of the series of images. The dynamic watermark timestamp and the DICOM metadata timestamp are compared and their mean difference or average difference (across the set of images) is used to determine the timestamp correction for the angiographic study. The DICOM timestamp may be corrected by the error, to generate corrected DICOM timestamp images 420 with second resolution.

However, DICOM timestamps have second resolution, and sub-second resolution is needed. To update the timestamp to include sub-second resolution, the watermark may be analyzed to obtain sub-second timing information.

Accordingly, corrected timestamp 430 is generated by combining the corrected DICOM timestamp 420 with sub-second timing based on the position of the rotational dials/radio-opaque markers cast onto the watermark. The timestamp is updated to include sub-second resolution not provided based on the DICOM timestamp.

This correction may be stored for subsequent use in correcting DICOM metadata timestamp with human clinical angiograms. The error may be determined before and after a human clinical angiogram to account for drift in DICOM metadata as a function of time (e.g., over days, weeks or even months). In some aspects, the corrected timestamp 430 may replace the DICOM timestamp, while in other aspects, the corrected timestamp 430 may be stored apart, in a different tag, from the DICOM timestamp.

Timestamp correction information (e.g., average error) may be saved in a computable readable format to permit subsequent synchronized calculations with other relevant data sources, such as physiological signals including an electrocardiogram that may be simultaneously obtained by separate hardware systems concurrent with the angiogram systems. These approaches may be used to synchronize data from systems without a real-time connection to the angiographic acquisition equipment to the data generated by the angiographic equipment. Thus, this approach provides for post hoc integration of an external signal (e.g., a cardiac signal) with the angiographic images to provide for applying reconstruction algorithms that offer spatiotemporal depictions of cardiac frequency activity, as taught by U.S. Pat. No. 10,123,761 ("the '761 patent").

FIG. 5 is a flowchart for generating a timestamp from dynamically watermarked x-ray images according to the techniques provided herein. In this example, while the DICOM timestamp may be present in the metadata, it is not utilized. Instead, only the watermarks from a plurality of time synced radio-opaque markers/dials are used to generate the timestamp. A suitable number of radio-opaque markers/dials are programmed to rotate at predefined frequencies to obtain the desired timestamp range and resolution (e.g., in terms of hours, minutes, seconds, sub-seconds, etc.).

Images 510 are obtained, with a watermark encoding timing information from a plurality of radio-opaque markers/dials, each radio-opaque marker/dial rotating at a different frequency. The watermarks are processed (e.g., according to FIG. 2 or FIG. 3), such that the rotational position of each radio-opaque marker/dial is determined. Based on the rotational position and the frequency of rotation of each radio-opaque marker/dial, a time for each radio-opaque marker/dial is determined, and the individual times are assembled into a timestamp with sub-second precision to generate the timestamp from time synced dials 520.

Figure 6:
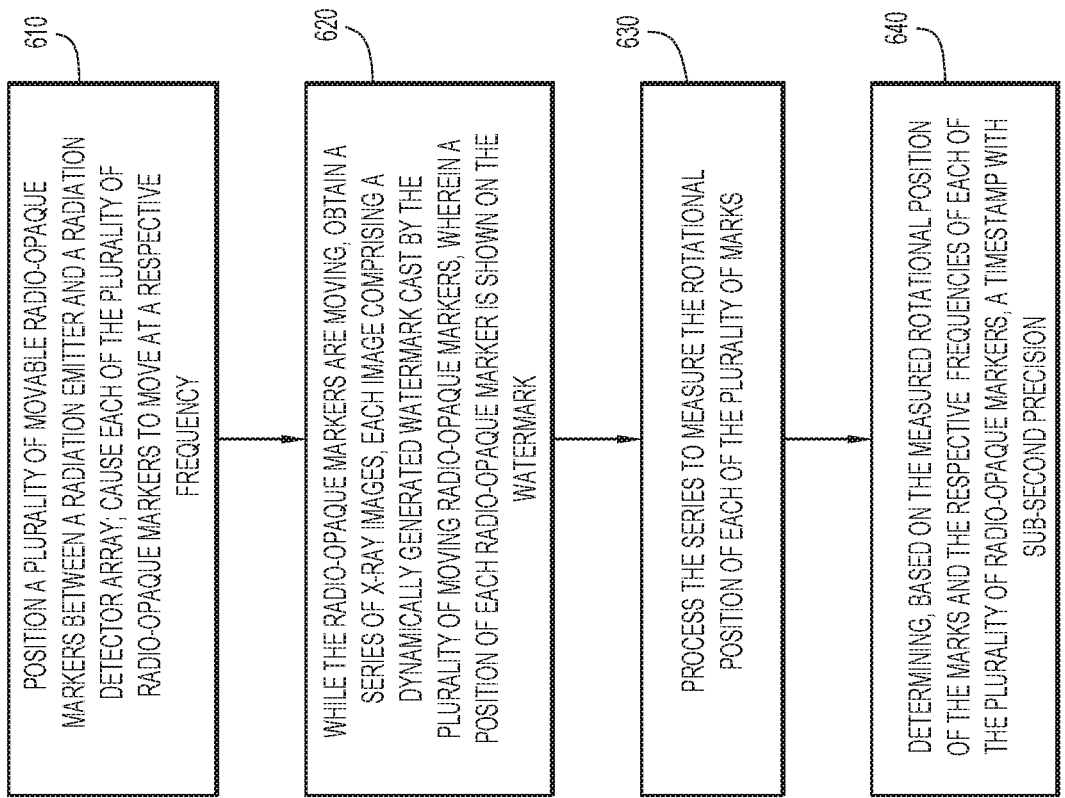
FIG. 6 is a high-level flow chart of operations for generating timestamps with sub-second precision based on dynamic watermarking of x-ray images, according to the techniques provided herein.

FIG. 6 is a high-level flow chart of operations for generating timestamps with sub-second precision based on dynamic timestamp watermarking of x-ray images, according to the techniques provided herein.

At operation 610, a plurality of movable radio-opaque markers is positioned between a radiation emitter and a radiation detector array. Each of the plurality of radio-opaque markers are caused to move at a respective frequency (e.g., by a controller).

At operation 620, while the radio-opaque markers are moving, a series of x-ray images are obtained, each image comprising a dynamically generated watermark cast by the plurality of moving radio-opaque markers, wherein a position of each radio-opaque marker is shown (e.g., as a mark) on the watermark. The watermark encodes a timestamp that may be decoded based on frequency and position.

At operation 630, the series is processed to measure rotational position of each of the plurality of marks cast onto the image. At operation 640, based on the measured rotational position of the marks and the respective frequency of each of the plurality of radio-opaque markers, a timestamp is determined with sub-second precision.

Advantages of the techniques provided herein include generation of an accurate timestamp, which allows an external signal to be synchronized with the angiographic images. Thus, by generating a correct timestamp, an external cardiac or other signal may be synchronized with the obtained images to increase the signal-to-noise ratio of obtained angiographic images (e.g., in conjunction with a cross-correlated wavelet algorithm that produces a spatiotemporal reconstruction of individual moving vascular pulse waves from the angiographic image sequence, as disclosed in the '761 patent).

This synchronization may be performed as part of a post hoc association process. Interpolation may be used, as needed, to fine tune synchronization of the timestamp of the images with the external signal.

Figure 7:
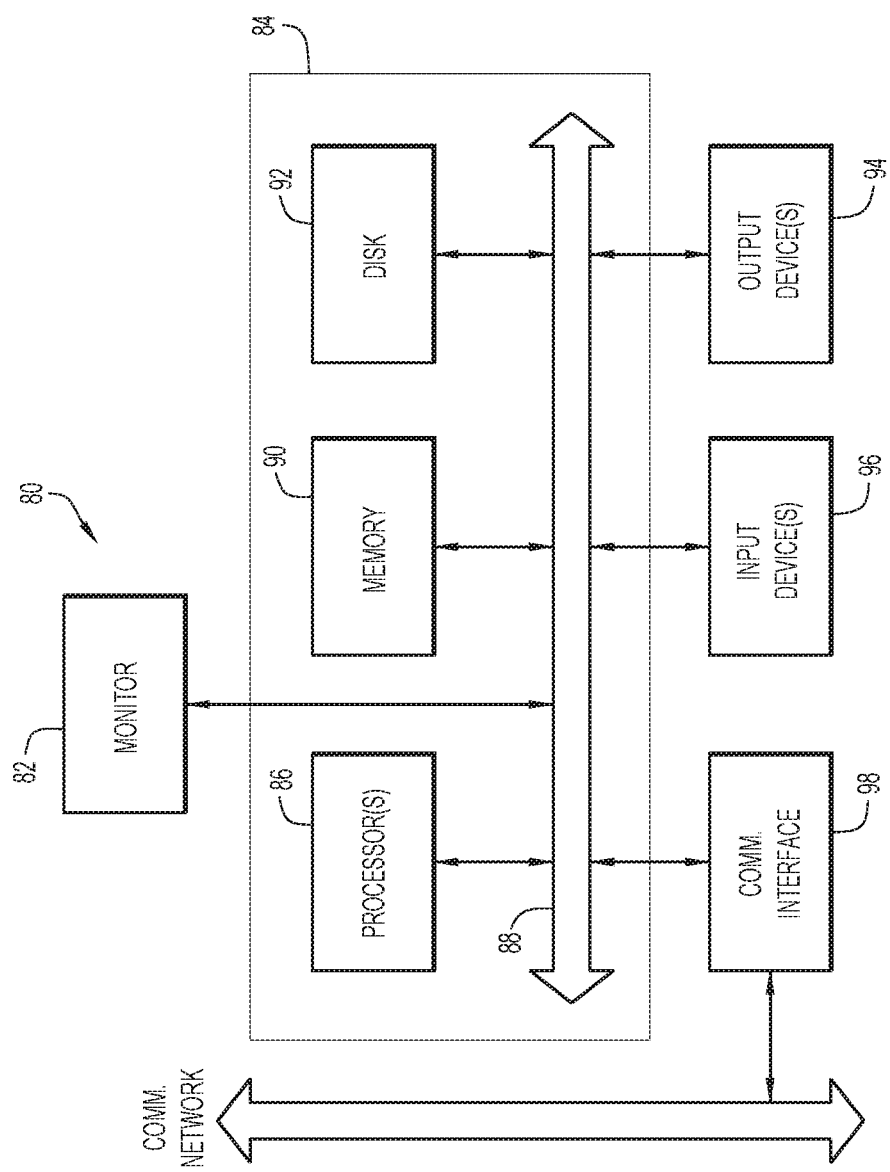
FIG. 7 is a block diagram of a computer system or information processing device that may be used with an angiographic system to store and analyze angiographic images comprising watermarks, according to the techniques provided herein.

FIG. 7 is a block diagram of a computer system or information processing device that may be used with embodiments of the invention. A computer system or information processing device 80 is illustrated that may be used with the system of FIGS. 1-6, 8 to obtain a series of watermarked angiographic images. Once obtained, the system may process the angiographic images to generate an accurate timestamp, according to any one or more of the techniques provided herein.

FIG. 7 is illustrative of a general-purpose computer system 80 programmed according to techniques within this disclosure or a specific information processing device for the embodiments provided herein, and is not intended to limit the scope of the subject matter disclosed herein. One of ordinary skill in the art would recognize other variations, modifications, and alternatives to computer system 80 that remain within the scope and equivalents of the disclosure.

In one embodiment, computer system 80 includes monitor 82, computer 84 (which includes processor(s) 86, bus subsystem 88, memory subsystem 90, and disk subsystem 92), user output devices 94, user input devices 96, and communications interface 98. Monitor 82 can include hardware and/or software elements configured to generate visual representations or displays of information. Some examples of monitor 82 may include familiar display devices, such as a television monitor, a cathode ray tube (CRT), a liquid crystal display (LCD), or the like. In some embodiments, monitor 82 may provide an input interface, such as incorporating touch screen technologies.

Computer 84 can include familiar computer components, such one or more central processing units (CPUs), memories or storage devices, graphics processing units (GPUs), communication systems, interface cards, or the like. As shown in FIG. 7, computer 84 may include one or more processor(s) 86 that communicate with a number of peripheral devices via bus subsystem 88. Processor(s) 86 may include commercially available central processing units or the like. Bus subsystem 88 can include mechanisms for letting the various components and subsystems of computer 84 communicate with each other as intended. Although bus subsystem 88 is shown schematically as a single bus, alternative embodiments of the bus subsystem may utilize multiple bus subsystems. Peripheral devices that communicate with processor(s) 86 may include memory subsystem 90, disk subsystem 92, user output devices 94, user input devices 96, communications interface 98, or the like.

Memory subsystem 90 and disk subsystem 92 are examples of physical storage media configured to store data. Memory subsystem 90 may include a number of memories including random access memory (RAM) for volatile storage of program code, instructions, and data during program execution and read only memory (ROM) in which fixed program code, instructions, and data are stored. Disk subsystem 92 may include a number of file storage systems providing persistent (non-volatile) storage for programs and data. Other types of physical storage media include floppy disks, removable hard disks, optical storage media such as CD-ROMS, DVDs and bar codes, semiconductor memories such as flash memories, read-only-memories (ROMS), battery-backed volatile memories, networked storage devices, or the like.

Memory subsystem 90 and disk subsystem 92 may be configured to store programming and data constructs that provide functionality or features of techniques discussed herein. Software code modules and/or processor instructions that when executed by processor(s) 86 implement or otherwise provide the functionality may be stored in memory subsystem 90 and disk subsystem 92.

User input devices 94 can include hardware and/or software elements configured to receive input from a user for processing by components of computer system 80. User input devices can include all possible types of devices and mechanisms for inputting information to computer system 84. These may include a keyboard, a keypad, a touch screen, a touch interface incorporated into a display, audio input devices such as microphones and voice recognition systems, and other types of input devices. In various embodiments, user input devices 94 can be embodied as a computer mouse, a trackball, a track pad, a joystick, a wireless remote, a drawing tablet, a voice command system, an eye tracking system, or the like. In some embodiments, user input devices 94 are configured to allow a user to select or otherwise interact with objects, icons, text, or the like that may appear on monitor 82 via a command, motions, or gestures, such as a click of a button or the like.

User output devices 96 can include hardware and/or software elements configured to output information to a user from components of computer system 80. User output devices can include all possible types of devices and mechanisms for outputting information from computer 84. These may include a display (e.g., monitor 82), a printer, a touch or force-feedback device, audio output devices, or the like.

Communications interface 98 can include hardware and/or software elements configured to provide unidirectional or bidirectional communication with other devices. For example, communications interface 98 may provide an interface between computer 84 and other communication networks and devices, such as via an internet connection.

FIG. 7 is representative of a computer system capable of embodying embodiments of the present invention. It will be readily apparent to one of ordinary skill in the art that many other hardware and software configurations are suitable for use with the present invention. For example, the computer may be a desktop, portable, rack-mounted or tablet configuration. Additionally, the computer may be a series of networked computers. In still other embodiments, the techniques described above may be implemented upon a chip or an auxiliary processing board.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, may fall there-between.

These embodiments have been described in terms of the preferred embodiment, and it is recognized that equivalents, alternatives, and modifications, aside from those expressly stated, are possible and within the scope of the appending claims.

What is claimed is:

1. A method of dynamic timestamp watermarking of x-ray images comprising:
    positioning a plurality of movable radio-opaque markers between a radiation emitter and a radiation detector array;
    causing each of the plurality of radio-opaque markers to move at a respective frequency; and
    while the radio-opaque markers are moving, obtaining a series of x-ray images, each image comprising a dynamically generated watermark cast by the plurality of moving radio-opaque markers, wherein a position of each radio-opaque marker is shown on the watermark.

2. The method of claim 1, further comprising:
    causing each of the plurality of radio-opaque markers to rotate at a respective frequency; and
    processing the series of images to measure a rotational position of each of the plurality of marks.

3. The method of claim 2, further comprising:
    determining, based on the measured rotational position and the respective frequency of each of the plurality of radio-opaque markers, a timestamp.

4. The method of claim 1, wherein the watermark encodes a timestamp with sub-second precision.

5. The method of claim 1, wherein each of the radio-opaque markers is in the form of a dial, and each of a plurality of dials are rotating at a rate determined by a controller synchronized to an international clock standard.

6. The method of claim 1, further comprising:
    decoding the watermark to generate a timestamp; and correcting a metadata timestamp based on the decoded timestamp.

7. The method of claim 1, wherein the radio-opaque marker is in the form of a dial and each of a plurality of dials include or is connected to a motor, the method further comprising:
rotating each motor at a different specified frequency so as to cause the associated dial to rotate at the same frequency.

8. The method of claim 1, wherein each of the radio-opaque markers is in the form of a dial, and at least two dials rotating at different frequencies are used to obtain sub-second precision.

9. The method of claim 1, wherein the radio-opaque markers are configured to rotate.

10. The method of claim 1, wherein each radio-opaque marker comprises a rotatable dial.

11. The method of claim 1, wherein the respective frequencies associated with the plurality of radio-opaque dials are different from each other.

12. A system for dynamic timestamp watermarking of an x-ray image, the system comprising:
a plurality of motors;
radio-opaque markers connected directly or indirectly to a motor, configured to selectively rotate responsively to operation of the plurality of motors; and
a controller configured to control operation of each of the plurality of motors to rotate each motor at a respective frequency, thereby causing the corresponding radio-opaque marker to rotate at the respective frequency;
one or more computer processors;
one or more computer readable storage media;
program instructions stored on the one or more computer readable storage media for execution by at least one of the one or more computer processors, the program instructions comprising instructions to:
process a series of x-ray images to generate a timestamp, wherein each image comprises a dynamically generated watermark encoding information corresponding to the timestamp, wherein the dynamically generated watermark is cast by the plurality of moving radio-opaque markers.

13. The system of claim 12, wherein each radio-opaque marker opacifies pixels from x-rays traveling from an x-ray source onto an x-ray detection array to form an image in a pixel array of a watermark.

14. The system of claim 12, wherein the program instructions further comprise instructions to cause the processor to:
compare the timestamp generated from the watermark to a timestamp contained in image metadata; and
correct a metadata timestamp associated with the image, obtained during human clinical angiograms, based on the timestamp generated from the watermark.

15. The system of claim 12, wherein the controller is synchronized to an international clock standard.

16. The system of claim 12, wherein at least two radio-opaque markers are used to obtain sub-second precision.

17. The system of claim 12, wherein at least three radio-opaque markers are used to encode a timestamp, and wherein the program instructions further comprise instructions to:
convert the timestamp into a timestamp having sub-second precision without using a metadata timestamp corresponding to the image.

18. A computer program product for determining a timestamp based on dynamic timestamp watermarking, the computer program product comprising one or more non-transitory computer readable storage media collectively having program instructions embodied therewith, the program instructions executable by a computer to cause the computer to:
obtain a series of x-ray images, each image comprising a dynamically generated watermark corresponding to a plurality of movable radio-opaque markers positioned between a radiation emitter and a radiation detector array, wherein a rotational position of each radio-opaque marker is cast onto the watermark as a mark, and wherein each radio-opaque marker is associated with a respective frequency; and
determine a rotational position of each of the plurality of marks.

19. The computer program product of claim 18, wherein the program instructions further cause the computer to:
determine, based on the measured rotational position and the known frequency of each of the plurality of marks of the watermark, a timestamp.

20. The computer program product of claim 19, wherein the timestamp has sub-second precision.

21. The computer program product of claim 18, wherein the watermark corresponds to a plurality of radio-opaque markers configured to rotate according to an international clock standard.

22. The computer program product of claim 18, wherein the program instructions further cause the computer to:
decode the watermark to generate a timestamp; and
correct a metadata timestamp based on the decoded timestamp.

23. The computer program product of claim 18, wherein the program instructions further cause the computer to:
determine a timestamp from a watermark corresponding to a plurality of radio-opaque markers, wherein each radio-opaque marker is rotated by a motor configured to cause the radio-opaque marker to rotate at a specified frequency.

* * * * *